(12) United States Patent
Garito et al.

(10) Patent No.: US 6,876,796 B2
(45) Date of Patent: Apr. 5, 2005

(54) NANOCOMPOSITE MICRORESONATORS

(75) Inventors: Anthony F. Garito, Radnor, PA (US);
Renyuan Gao, Wayne, PA (US);
Renfeng Gao, Phoenixville, PA (US);
Yu-Ling Hsiao, Collegeville, PA (US);
Jingsong Zhu, Phoenixville, PA (US)

(73) Assignee: Photon-X, LLC, Malvern, PA (US)

( * ) Notice: Subject to any disclaimer, the term of this patent is extended or adjusted under 35 U.S.C. 154(b) by 0 days.

(21) Appl. No.: 10/354,095

(22) Filed: Jan. 30, 2003

(65) Prior Publication Data
US 2004/0150268 A1 Aug. 5, 2004

Related U.S. Application Data
(60) Provisional application No. 60/353,095, filed on Jan. 30, 2002.

(51) Int. Cl.[7] .................................................. G02B 6/26
(52) U.S. Cl. .............................. 385/50; 385/24; 385/30; 385/142
(58) Field of Search ............................. 385/50, 24, 27, 385/30–32, 142–146

(56) References Cited

U.S. PATENT DOCUMENTS

| | | | |
|---|---|---|---|
| 5,825,799 A | 10/1998 | Ho et al. ................... 372/92 |
| 6,052,495 A | 4/2000 | Little et al. .................. 385/2 |
| 6,078,605 A | 6/2000 | Little et al. ................ 372/94 |
| 6,101,300 A | 8/2000 | Fan et al. ................... 385/27 |
| 6,130,969 A | 10/2000 | Villeneuve et al. .......... 385/27 |
| 6,195,187 B1 | 2/2001 | Soref et al. .................. 398/9 |
| 6,292,292 B1 * | 9/2001 | Garito et al. ............ 359/341.5 |
| 6,304,689 B1 | 10/2001 | Dingel et al. ................ 385/24 |
| 6,411,752 B1 * | 6/2002 | Little et al. .................. 385/17 |

OTHER PUBLICATIONS

Chen et al., "Silicon Photonic Band Gap, Microcavity and Waveguide Structures," Electronic Materials Research Group (Mar. 26, 2002), pp. 1–11.
Liu et al., "Passive microring–resonator–coupled lasers," Applied Physics Letters (Nov. 26, 2001), 79:3561–63.
Absil et al., "Vertically Coupled Microring Resonators Using Polymer Wafer Bonding," IEEE Photonics Technology Letters (1/01), 13:49–51.
Laine et al., "Microsphere Resonator Mode Characterization by Pedestal Anti–Resonant Reflecting Waveguide Coupler," IEEE Photonics Technology Letters (8/00), 12:1004–06.
Little et al., "Theory of Loss and Gain Trimming of Resonator–Type Filters," IEEE Photonics Technology Letters (6/00), 12:636–638.
Little et al., "Theory of Polarization Rotation and Conversion in Vertically Coupled Microresonatros," IEEE Photonics Technology Letters (4/00), 12:401–403.
Hryniewich et al., "Higher Order Filter Response in Coupled Microring Resonators," IEEE Photonics Technology Letters (3/00), 12:320–322.

(Continued)

Primary Examiner—Michael G. Lee
Assistant Examiner—Seung H Lee
(74) Attorney, Agent, or Firm—Min, Hsieh & Hack LLP

(57) ABSTRACT

A microresonator is provided that incorporates a composite material comprising a polymer matrix and nanoparticles dispersed therein. The microresonator includes the composite material having a shape that is bounded at least in part by a reflecting surface. The shape of the microresonator allows a discrete electromagnetic frequency to set up a standing wave mode. Advantageously, the polymer matrix comprises at least one halogenated polymer and the dispersed nanoparticles comprise an outer coating layer, which may also comprise a halogenated polymer. Methods for making composite materials and microresonators are also provided. Applications include, for example, active and passive switches, add/drop filters, modulators, isolators, and integrated optical switch array circuits.

91 Claims, 8 Drawing Sheets

OTHER PUBLICATIONS

Chu et al., "Cascaded Microring Resonators for Crosstalk Reduction and Spectrum Cleanup in Add–Drop Filters," IEEE Photonics Technology Letters (11/99), 11:1423–25.

Chu et al., "Second–Order Filter Response From Parallel Coupled Glass Microring Resonators," IEEE Photonics Technology Letters (11/99), 11:1426–28.

Laine et al., "Etch–Eroded Fiber Coupler for Whispering–Gallery–Mode Excitation in High–Q Silica Microsperes," IEEE Photonics Technology Letters (11/99), 11:1429–30.

Chu et al., "Temperature Insensitive Vertically Coupled Microring Resonator Add/Drop Filters by Means of a Polymer Overlay," IEEE Photonics Technology Letters (9/99), 11:1138–40.

Vardeny et al., "Stimulated Emission and Lasing in π–Conjugated Polymer Films, Microsctructures and Opal Photonic Crystals," SPIE Conference on Organic Light–Emitting Materials and Devices III (7/99), pp. 2–16.

Chu et al., "Wavelength Trimming of a Microring Resonator Filter by Means of a UL Sensitive Polymer Overlay," IEEE Photonics Technology Letters (6/99), 11:688–690.

Chu et al., "An Eight–Channel Add–Drop Filter Using Vertically Coupled Microring Resonators over a Cross Grid," IEEE Photonics Technology Letters (6/99), 11:691–693.

Chu et al., "ARROW–Type Vertical Coupler Filter: Design and Fabrication," Journal of Lightwave Technology (4/99), 17:652–658.

Little et al., "Analytic Theory of Coupling from Tapered Fibers and Half–Blocks into Microsphere Resonators," Journal of Lightwave Technology (4/99), 17:704–715.

Rhodes, "NSOM of Guided Waves," SC770 Guided–Wave Optoelectronics (1999), pp. 1–2.

Chin et al., "Modeling and design of waveguide–coupled single–mode micro–ring resonators," SPIE (9/98), 3551:36–48.

Soref et al., "Proposed N–Wavelength M–Fiber WDM crossconect Switch Using Active Microring Resonators," IEEE Photonics Technology Letters (8/98), 10:1121–23.

Fan et al., "Channel drop filters in photonic crystals," Optics Express (7/98), pp. 1–2.

Little et al., "Wavelength Switching and Routing Using Absorption and Resonance," IEEE Photonics Technology Letters (6/98), 10:816–818.

Little et al., "Ultra–Compact Si–$SiO_2$ Microring Resonator Optical Channel Dropping Filters," IEEE Photonics Technology Letters (4/98), 10:549–551.

Little et al., "Nondegenerate Four–Wave Mixing Efficiencies in DFB Laser Wavelength Converters," IEEE Photonics Technology Letters (4/98), 10:519–521.

Chu et al., "Reduction of Filter Sidelobe Level by an X–Crossing Vertical Coupled ARROW Filter," IEEE Photonics Technology Letters (3/98), 10:391–393.

Little et al., "Design Rules for Maximally Flat Wavelength–Insensitive Optical Power Dividers Using Mach–Zehnder Structures," IEEE Photoncis Technology Letters (12/97), 9:1607–09.

Rafizadeh et al., "Waveguide–coupled AIGaAs/GaAs microcavity ring and disk r sonators with high finesse and 21.6–nm free spectral range," Optics Letters (8/97), 22:1244–46.

Little, "Filter Synthesis for Coupled Waveguides," Journal of Lightwave Technology (7/97), 15:1149–55.

Little et al., "Microring Resonator channel Dropping Filters," Journal of Lightwave Technology (6/97), 15:998–1005.

Rafizadeh et al., "Temperature tuning of microcavity ring and disk resonators at 1.5–$\mu$m," IEEE Lasers and Electro–Optics Society (11/97), pp. 162–163.

Little et al., "Window Functions for Ideal Response in Distributed Feedback Reflection Filters," IEEE Photonics Technology Letters (1/97), 9:76–78.

Little, "A Variational Coupled–Mode Theory Including Radiation Loss for Grating–Assisted Couplers," Journal of Lightwave Technology (2/96), 14:188–195.

Little et al., "A Variational Coupled–Mode Theory for Periodic Waveguides," IEEE Journal of Quantum Electronics (12/95), 31:2258–64.

Little, "Intensity–Induced Stopband Bending in Periodic Nonlinear Multilayers," IEEE Journal of Quantum Electronics (11/94), 30:2589–96.

Little, "Optical Induced Spectral Tuning in Grating–Assisted Nonlinear Couplers," Journal of Lightwave Technology (5/94), 12:774–783.

Huang et al., "On Phase Matching and Power Coupling in Grating–Assisted Couplers," IEEE Photonics Technology Letters (2/92), 4:151–153.

Huang et al., "Optical Wavelength Filter with Tapered Couplers," IEEE Photonics Technology Letters (9/91), 3:809–812.

Huang et al., "Power Exchange in Tapered Optical Couplers," IEEE Journal of Quantum Electronics (7/91), 27:1932–38.

\* cited by examiner

NANOCOMPOSITE MICRORESONATORS

CROSS-REFERENCE TO RELATED APPLICATION

This application claims the benefit of priority under 35 U.S.C. § 119(e) to U.S. Provisional Application Ser. No. 60/353,095, filed Jan. 30, 2002.

FIELD OF THE INVENTION

The present invention relates to microresonators, such as microrings, microdisks, microspheres, microplates, and microlines made from random glassy matrix materials and nanoparticles distributed within the matrix.

BACKGROUND

All-optical switching between waveguides in dense-wavelength-division multiplexed (hereinafter, "WDM") networks using microring resonators is well known. However, such switching is limited by optical loss effects. For example, a microring resonator made of an electroabsorptive material coupled to two straight semiconductor side-channel waveguides has been proposed that could operate as a 2×2 crosspoint switch when the rings were switched from a low-absorption state to a high-absorption state. See, Soref et al. "Proposed. N-Wavelength M-Fiber WDM Crossconnect Switch Using Active Microring Resonators" *IEEE Phontonics Technology Letters,* Vol. 10, No. 8, (August 1998), which is hereby incorporated by reference in its entirety. As described by Soref et al., the rings could be made of layered III–V semiconductor heterostructure materials, and individual cross-points can be made of two-ring devices. Nonetheless, material loss, waveguide bending loss, and related fabrication-technology related losses, such as wall-roughness that occurs during waveguide etching, are known to limit optical switch performance.

Another challenge facing the implementation of integrated optical chip applications is the extremely small sizes required to make these waveguide devices commercially viable. To make microrings sufficiently small for intergrated optical chip applications, they require very large refractive index differences between the core material and the cladding material. Unfortunately, a large refractive index difference typically exhibits large scattering from sidewall imperfections, which causes large attenuation level. See, Little et al. "Microring Resonator Channel Dropping Filters," *Journal of Lightwave Technology,* Vol. 15, No. 6 (June 1997) (hereinafter, "Little et al."). If an appropriate optical material could be formulated for making a waveguide, coupling that waveguide to a microresonator could still be problematic. For example, to couple a conventional silica waveguide to a silica microsphere resonator, the waveguide typically is clad with materials of significantly lower refractive index to avoid leakage of radiation modes into the cladding. Because cladding materials having refractive indices that are less than silica (e.g., the material forming the microresonator) are not readily available, it is believed that basic waveguide coupling schemes have been frustrated. See, Laine et al. "Microsphere Resonator Mode Characterization by Pedestal Anti-Resonant Reflecting Waveguide Coupler" *IEEE Photonics Technology Letters,* Vol. 12, No. 8, at 1004 (August 2000), which is hereby incorporated by reference in its entirety. It is well established that in a waveguide structure, such as a microring resonator, aside from coupling losses, the total waveguide loss, which includes contributions from waveguide side walls, bends, and material losses, should be approximately equal to, or less than, 0.5 dB/cm in maganitude, and preferably less than 0.2 dB/cm. For a highly transparent optical medium to be used as the waveguide material, a fundamental requirement is that the medium exhibits little, or no, absorption and scattering losses. Intrinsic absorption losses commonly result from the presence of fundamental excitations that are electronic, vibrational, or coupled electronic-vibrational modes in origin. Further, the device operating wavelength of the microring resonator should remain largely different from the fundamental, or overtone, wavelengths for these excitations, especially in the case of the telecommunication wavelengths of 850, 1310, and 1550 nm located in the low loss optical window of a standard silica glass optical fiber, or waveguide. Material scattering losses occur when the signal wave encounters abrupt changes in refractive index of the otherwise homogeneous uniform optical medium. These discontinuities can result from the presence of composition inhomogenieties, crystallites, microporous structures, voids, fractures, stresses, faults, or even foreign impurities such as dust or other particulates.

In a waveguide structure comprised of a uniform square, or circular, waveguide cross-section, the waveguide material should exhibit little, or no, polarization dependence in signal propagation through the material. A potential source for polarization dependent behavior is the birefringence of the waveguide material. Birefringence is quantified by the difference in the refractive indexes for different polarization states for the propagating waveguide signal. The origin of material birefringence can be either intrinsic such as from the atomic structure or morphology of the material, or extrinsic such as from the effects of induced, or externally applied, force fields, or both. Composite materials are also well known, and generally comprise two or more materials each offering its own set of properties or characteristics. The two or more materials may be joined together to form a system that exhibits properties derived from each of the materials. A common form of a composite is one with a body of a first material (a matrix) with a second material distributed in the matrix.

One class of composite materials includes nanoparticles distributed within a host matrix material. Nanoparticles are particles of a material that have a size measured on a nanometer scale. Generally, nanoparticles are larger than a cluster (which might be only a few hundred atoms in some cases), but with a relatively large surface area-to-bulk volume ratio. While most nanoparticles have a size from about 10 nm to about 500 nm, the term nanoparticles can cover particles having sizes that fall outside of this range. For example, particles having a size as small as about 1 nm and as large as about $1\times10^3$ nm could still be considered nanoparticles. Nanoparticles can be made from a wide array of materials. Among these materials examples include metal, glass, ceramics, refractory materials, dielectric materials, carbon or graphite, natural and synthetic polymers including plastics and elastomers, dyes, ion, alloy, compound, composite, or complex of transition metal elements, rare-earth metal elements, group VA elements, semiconductors, alkaline earth metal elements, alkali metal elements, group IIIA elements, and group IVA elements Further, the materials may be crystalline, amorphous, or mixtures, or combinations of such structures.

Moreover, nanoparticles themselves may be considered a nanoparticle matrix, which may comprise a wide array of materials, single elements, mixtures of elements, stoichiometric or non-stoichiometric compounds The host matrix may be comprised of a random glassy matrix such as an inorganic glass, or organic polymer.

Suitable inorganic glass hosts include but are not limited to doped and undoped silica such as aluminosilicate glasses, silica, germania-silica, lithium-alumina-silica, sulfide glasses, phosphate glasses, halide glasses, oxide glasses, and chalcogenide glasses. Organic polymers may include typical hydrocarbon polymers and halogenated polymers.

By introducing nanoparticles into the core of the waveguide structure, the absorption and scattering losses due to the nanoparticles may add to the waveguide propagation loss. In order to keep the waveguide propagation loss to a minimum, in addition to controlling the loss contribution from the waveguide host matrix, it is essential to control the absorption and scattering loss from the nanoparticles doped into the waveguide core.

For discrete nanoparticles that are approximately spherical in shape and doped into the host matrix, the scattering loss $\alpha$, in dB per unit length, resulting from the presence of the particles is dependent on the particle diameter d, the refractive index ratio of the nanoparticles and the waveguide core $m = n_{par}/n_{core}$, and the volume fraction of the nanoparticles in the host waveguide core $V_p$. The nanoparticle induced scattering loss can be calculated by:

$$\alpha = 1.692 \times 10^3 \left(\frac{m^2 - 1}{m^2 + 2}\right)^2 \frac{d^3 V_p}{\lambda^4}, \quad (1)$$

where $\lambda$ is the vacuum propagation wavelength of the light guided inside the waveguide. As an example, when m=2, $V_p$=10%, $\lambda$=1550 nm, d=10 nm, the calculated scattering loss $\alpha$ is 0.07 dB/cm. To fabricate a certain waveguide device with a set loss specification, and therefore a nanoparticle induced waveguide loss budget of $\alpha$, the nanoparticle diameter d must satisfy the following relationship:

$$d < \left(\alpha \frac{1}{1.692 \times 10^3} \left(\frac{m^2 + 2}{m^2 - 1}\right)^2 \frac{\lambda^4}{V_p}\right)^{1/3}, \quad (2)$$

where $\lambda$ is the vacuum propagation wavelength of the light guided inside the waveguide, $m = n_{par}/n_{core}$ the refractive index ratio of the nanoparticles and the core, and $V_p$ the volume fraction of the nanoparticles in the host waveguide core. For example, following Equation 2, with a nanoparticle loss budget of $\alpha$=0.5 dB/cm, when m=2, $V_p$=10%, $\lambda$=1550 nm, the nanoparticle diameter d must be smaller than 19 nm. In general, the diameter of the nanoparticles must be smaller than 50 nm, and more preferably, 20 nm.

Nanocomposite materials including nanoparticles distributed within a host matrix material have been used in optical applications. For example, U.S. Pat. No. 5,777,433 (the '433 patent) discloses a light emitting diode (LED) that includes a packaging material including a plurality of nanoparticles distributed within a host matrix material. The nanoparticles increase the index of refraction of the host matrix material to create a packaging material that is more compatible with the relatively high refractive index of the LED chip disposed within the packaging material. Because the nanoparticles do not interact with light passing through the packaging material, the packaging material remains substantially transparent to the light emitted from the LED.

While the packaging material used in the '433 patent offers some advantages derived from the nanoparticles distributed within the host matrix material, the composite material of the '433 patent remains problematic. For example, the composite material of the '433 patent includes glass or ordinary hydrocarbon polymers, such as epoxy and plastics, as the host matrix material. While these materials may be suitable in certain applications, they limit the capabilities of the composite material in many other areas. For example, the host matrix materials of the '433 patent commonly exhibit high absorption losses.

Additionally, the method of the '433 patent for dealing with agglomeration of the nanoparticles within the host matrix material is inadequate for many composite material systems. Agglomeration is a significant problem when making composite materials that include nanoparticles distributed within a host matrix material. Because of the small size and great numbers of nanoparticles that may be distributed within a host matrix material, there is a large amount of interfacial surface area between the surfaces of the nanoparticles and the surrounding host matrix material. As a result, the nanoparticle/host-matrix material system operates to minimize this interfacial surface area, and corresponding surface energy, by combining the nanoparticles together to form larger particles. This process is known as agglomeration. Once the nanoparticles have agglomerated within a host matrix material, it is extremely difficult to separate the agglomerated particles back into individual nanoparticles.

Agglomeration of the nanoparticles within the host matrix material may result in a composite material that lacks a desired characteristic. Specifically, when nanoparticles agglomerate together, the larger particles formed may not behave in a similar way to the smaller nanoparticles. For example, while nanoparticles may be small enough to avoid scattering light within the composite material, agglomerated particles may be sufficiently large to cause scattering. As a result, a host matrix material may become substantially less transparent in the presence of such agglomerated particles.

To combat agglomeration, the composite material of the '433 patent includes an anti-flocculant coating disposed on the nanoparticles intended to inhibit agglomeration. Specifically, the '433 patent suggests using surfactant organic coatings to suppress agglomeration. These types of coatings, however, may be inadequate or ineffective especially when used with host matrix materials other than typical hydrocarbon polymers.

It would therefore be desirable to overcome one or more of the problems or disadvantages associated with the prior art.

SUMMARY OF THE INVENTION

The present invention is directed to a microresonantor comprising a nanocomposite material. The nanocomposite material includes a host matrix and nanoparticles dispersed within the matrix. The host matrix comprises inorganic or organic random glassy media. The nanoparticles may include an outer layer, advantageously, one that is compatible with the host matrix. Thus, for example, when the matrix comprises an organic polymer, the outer coating layer may also be organic. Consistent with the present invention the microresonator has a shape sufficient to allow electromagnetic radiation having a discrete frequency to set up a standing wave mode, the shape chosen from a microring, a microdisk, a microsphere, a microplate, and a microline.

The nanocomposite material according to the present invention can have a number of beneficial optical properties, including a high refractive index and a high transmission.

While a random glassy medium may be used in the host matrix, consistent with one embodiment of the present invention, the matrix comprises at least one organic polymer.

While a random glassy medium may be used in the host matrix, consistent with one embodiment of the present invention, the matrix comprises at least one inorganic glass.

In addition, the nanocomposite material according to the present invention comprises nanoparticles, which may be coated or bare. When coated with a polymer, the particles may also contain at least one halogenated polymer.

It is to be understood that the foregoing general description and the following detailed description are exemplary and explanatory only and are not restrictive of the invention, as claimed.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION OF THE INVENTION

In the following description, reference is made to the accompanying drawings that form a part thereof, and in which is shown by way of illustration specific exemplary embodiments in which the invention can be practiced. These embodiments are described in sufficient detail to enable those skilled in the art to practice the invention, and it is to be understood that other embodiments can be utilized and that changes can be made without departing from the scope of the present invention.

Figure 1:
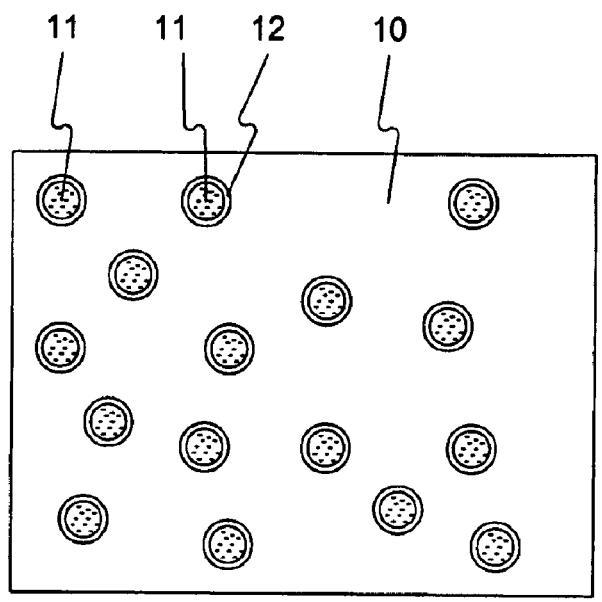
FIG. 1 depicts a schematic representation of an exemplary nanocomposite material according to one embodiment of the invention.

FIG. 1 provides, a schematic representation of a nanocomposite material according to an embodiment of the invention. The nanocomposite material includes a random glassy matrix 10 and plurality of nanoparticles 11 dispersed either uniformly or non-uniformly within matrix 10. While FIG. 1 shows the plurality of nanoparticles 11 including an outer coating layer 12, which at least partially coats nanoparticles 11 and inhibits their agglomeration, depending on the specific properties desired and/or host matrix used, the particles may be uncoated or bare.

As shown in FIG. 1, the nanoparticles may include an outer layer 12. As used herein, the term layer is a relatively thin coating on the outer surface of an inner core (or another inner layer) that is sufficient to impart different characteristics to the outer surface. The layer need not be continuous or thick to be an effective layer, although it may be both continuous and thick in certain embodiments.

In one embodiment, the polymer matrix 10 can comprise a halogenated elastomer, a perhalogenated elastomer, a halogenated plastic, or a perhalogenated plastic, either by itself or in a blend with other matrix material listed herein.

In another embodiment, the polymer matrix 10 may comprise a polymer, a copolymer, or a terpolymer having at least one halogenated monomer represented by one of the following formulas:

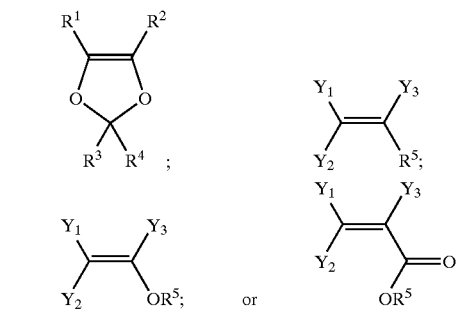

wherein $R^1$, $R^2$, $R^3$, $R^4$, and $R^5$, which may be identical or different, are each chosen from linear or branched hydrocarbon-based chains, possibly forming at least one carbon-based ring, being saturated or unsaturated, wherein at least one hydrogen atom of the hydrocarbon-based chains may be halogenated; a halogenated alkyl, a halogenated aryl, a halogenated cyclic alky, a halogenated alkenyl, a halogenated alkylene ether, a halogenated siloxane, a halogenated ether, a halogenated polyether, a halogenated thioether, a halogenated silylene, and a halogenated silazane. $Y_1$ and $Y_2$, which may be identical or different, are each chosen from H, F, Cl, and Br atoms. $Y_3$ is chosen from H, F, Cl, and Br atoms, $CF_3$, and $CH_3$.

Alternatively, the polymer may comprise a condensation product made from the monomers listed below:

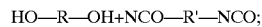

or

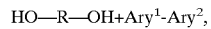

wherein R, R', which may be identical or different, are each chosen from halogenated alkylene, halogenated siloxane, halogenated ether, halogenated silylene, halogenated arylene, halogenated polyether, and halogenated cyclic alkylene. $Ary^1$, $Ary^2$, which may be identical or different, are each chosen from halogenated aryls and halogenated alkyl aryls.

Ary as used herein, is defined as being a saturated, or unsaturated, halogenated aryl, or a halogenated alkyl aryl group.

Alternatively, the polymer matrix 10 can comprise a halogenated cyclic olefin polymer, a halogenated cyclic olefin copolymer, a halogenated polycyclic polymer, a halogenated polyimide, a halogenated polyether ether ketone, a halogenated epoxy resin, a halogenated polysulfone, or halogenated polycarbonate.

In certain embodiments, the polymer matrix 10, for example, a fluorinated polymer host matrix 10, may exhibit very little absorption loss over a wide wavelength range. Therefore, such fluorinated polymer materials may be suitable for optical applications.

In one embodiment, the halogenated aryl, alkyl, alkylene, alkylene ether, alkoxy, siloxane, ether, polyether, thioether, silylene, and silazane groups are at least partially halogenated, meaning that at least one hydrogen in the group has been replaced by a halogen. In another embodiment, at least one hydrogen in the group may be replaced by fluorine. Alternatively, these aryl, alkyl, alkylene, alkylene ether, alkoxy, siloxane, ether, polyether, thioether, silylene, and silazane groups may be completely halogenated, meaning that each hydrogen of the group has been replaced by a halogen. In an exemplary embodiment, the aryl, alkyl, alkylene, alkylene ether, alkoxy, siloxane, ether, polyether, thioether, silylene, and silazane groups may be completely fluorinated, meaning that each hydrogen has been replaced by fluorine. Furthermore, the alkyl and alkylene groups may include between 1 and 12 carbon atoms.

Additionally, polymer matrix 10 may comprise a combination of one or more different halogenated polymers, such as fluoropolymers, blended together. Further, polymer matrix 10 may also include other polymers, such as halogenated polymers containing functional groups such as phosphinates, phosphates, carboxylates, silanes, siloxanes, sulfides, including POOH, POSH, PSSH, OH, $SO_3H$, $SO_3R$, $SO_4R$, COOH, $NH_2$, NHR, $NR_2$, $CONH_2$, NH—$NH_2$, and others, where R may comprise any of aryl, alkyl, alkylene, siloxane, silane, ether, polyether, thioether, silylene, and silazane. Further, polymer matrix 10 may also include homopolymers or copolymers of vinyl, acrylate, methacrylate, vinyl aromatic, vinyl esters, alpha beta unsaturated acid esters, unsaturated carboxylic acid esters, vinyl chloride, vinylidene chloride, and diene monomers. Further, the polymer matrix may also include a hydrogen-containing fluoroelastomer, a hydrogen-containing perfluoroelastomer, a hydrogen containing fluoroplastic, a perfluorothermoplastic, at least two different fluoropolymers, or a cross-linked halogenated polymer.

Examples of the polymer matrix 10 include: poly[2,2-bistrifluoromethyl-4,5-difluoro-1,3-dioxole-co-tetrafluoroethylene], poly[2,2-bisperfluoroalkyl-4,5-difluoro-1,3-dioxole-co-tetrafluoroethylene], poly[2,3-(perfluoroalkenyl) perfluorotetrahydrofuran], poly[2,2,4-trifluoro-5-trifluoromethoxy-1,3-dioxole-co-tetrafluoroethylene], poly(pentafluorostyrene), fluorinated polyimide, fluorinated polymethylmethacrylate, polyfluoroacrylates, polyfluorostyrene, fluorinated polycarbonates, fluorinated poly (N-vinylcarbazole), fluorinated acrylonitrile-styrene copolymer, fluorinated Nafion®, and fluorinated poly(phenylenevinylene). The polymer matrix 10 may further include inactive fillers, for example silica.

Additionally, the polymer matrix may comprise any polymer sufficiently clear for optical applications. Examples of such polymers include polymethylmethacrylates, polystyrenes, polycarbonates, polyimides, epoxy resins, cyclic olefin copolymers, cyclic olefin polymers, acrylate polymers, PET, polyphenylene vinylene, polyether ether ketone, poly (N-vinylcarbazole), acrylonitrile-styrene copolymer, Nafion®, poly(phenylenevinylene), polyfluoroacrylates, fluorinated polycarbonates, perfluoropolycyclic polymers, fluorinated cyclic olefins, or fluorinated copolymers of cyclic olefins.

By including halogens, such as fluorine, into polymer matrix 10, the optical properties of polymer matrix 10 and the resulting nanocomposite material are improved over conventional nanocomposite materials. Unlike the C—H bonds of hydrocarbon polymers, carbon-to-halogen bonds (such as C—F) shift the vibrational overtones toward longer wavelengths out of the ranges used in telecommunication applications. For example, the carbon-to-halogen bonds exhibit vibrational overtones having low absorption levels ranging, especially the telecommunication wavelengths around 850, 1310, and 1550 nm. As hydrogen is removed through partial to total halogenation, the absorption of light by vibrational overtones is reduced. One parameter that quantifies the amount of hydrogen in a polymer is the molecular weight per hydrogen for a particular monomeric unit. For highly halogenated polymers useful in optical applications, this ratio may be 100 or greater. This ratio approaches infinity for perhalogenated materials.

Nanoparticles 11 may comprise various different materials, and they may be fabricated using several different methods. In one embodiment of the invention, the nanoparticles are produced using an electro-spray process. In this process, very small droplets of a solution including the nanoparticle precursor material emerge from the end of a capillary tube, the end of which is maintained at a high positive or negative potential. The large potential and small radius of curvature at the end of the capillary tube creates a strong electric field causing the emerging liquid to leave the end of the capillary as a mist of fine droplets. A carrier gas captures the fine droplets, which are then passed into an evaporation chamber. In this chamber, the liquid in the droplets evaporates and the droplets rapidly decrease in size. When the liquid is entirely evaporated, an aerosol of nanoparticles is formed. These particles may be collected to form a powder or they may be dispersed into a solution. The size of the nanoparticles is variable and depends on processing parameters.

In an exemplary embodiment of the present invention, nanoparticles 11 have a major dimension of less than about 50 nm. That is, the largest dimension of the nanoparticle (for example the diameter in the case of a spherically shaped particle) is less than about 50 nm. Other processes are also useful for making nanoparticles 11 of the present invention. For example, nanoparticles 11 can be fabricated by laser ablation, laser-driven reactions, flame and plasma processing, solution-phase synthesis, sol-gel processing, spray pyrolysis, mechanochemical processing, sono-electro chemistry, physical vapor deposition, hydrothermal methods, vacuum deposition, or any other suitable method for obtaining particles having appropriate dimensions and characteristics.

Because many semiconductor materials have refractive index values between about 2 and about 5, these materials can be used to tune the refractive index of the nanocomposite materials for optical applications, such as waveguides and microresonators. Thus, semiconductor materials may also be used to form nanoparticles 11. These materials include, for example, Si, Ge, SiGe, GaP, GaAs, InP, InAs, InSb, ZnS, PbS, PbSe, PbTe, and other semiconductor materials, as well as their counterparts doped with a rare-earth or transition metal ions. Still other materials such as inorganic salts, oxides or compounds can be used to tune the refractive index of the nanocomposite materials for optical applications, such as waveguides and microresonators. For example lithium niobate, barium titinate, proustite, yttrium aluminate, rutile, and ziroconate and other related materials, as well as their counterparts doped with a rare-earth or transition metal ions.

Several classes of materials may be used to form nanoparticles 11 depending upon the effect the nanoparticles are to have on the properties of the nanocomposite containing them. In one embodiment, nanoparticles 11 may include one or more active materials, which allow the nanocomposite to be a gain medium. Active materials amplify a light signal as the light signal encounters the active material. Active materials may include transition metal elements, rare-earth metal elements, group VA elements, semiconductors, and group IVA elements in the forms of ions, alloys, compounds, composites, complexes, chromophores, dyes or polymers. Rare-earth as used herein is understood to include those known to one skilled in the art, and include Yttrium and Scandium. Active materials also include $V^{2+}$, $V^{3+}$, $Cr^{3+}$, $Cr^{4+}$, $Co^{2+}$, $Fe^{2+}$, $Ni^{2+}$, $Ti^{3+}$, and $Bi^{3+}$.

The material that forms the matrix of nanoparticle 11 may be in the form of an ion, alloy, compound, or complex, and may comprise the following: an oxide, phosphate, halophosphate, phosphinate, arsenate, sulfate, borate, aluminate, gallate, silicate, germanate, vanadate, niobate, tantalate, tungstate, molybdate, alkalihalogenate, halogenide, nitride, selenide, sulfide, sulfoselenide, tetrafluoroborate, hexafluorophosphate, phosphonate, and oxysulfide.

Metal containing materials such as metal chalcogenides (e.g., $Bi_2Te_3$, $Bi_2Te_3$), metal salts, transition metals, transition metal complexes, transition metal containing compounds, transition metal oxides, and organic dyes, such as, for example, Rodamin-B, DCM, Nile red, DR-19, and DR-1, and polymers may be used. ZnS, or PbS doped with a rare-earth or transition metal for optical amplification can also be used to form nanoparticles. Additionally, oxides such as $TiO_2$ and $SiO_2$ may also be used.

In one embodiment, the nanoparticles are coated with a polymer, such as a halogenated polymer. In certain embodiments, the coated nanoparticles comprise one or more active materials. Coated nanoparticles comprising active materials find particular utility as low phonon energy gain media.

In one particular application, a nanocomposite material can be fabricated that has a high refractive index and minimal absorption loss. For example, halogenated polymers, including fluorinated polymers, exhibit very little absorption loss. Therefore, these halogenated polymers can be particularly suitable for transmitting light in optical waveguides and other devices. For example, spherically shaped nanoparticles 11 can be formed such that their diameters are smaller than 50 nm, more preferably smaller than 20 nm. As a result, the presence of nanoparticles 11 dispersed within the matrix material 10 (in the case of the example, a halogenated polymer) causes little, or no, scattering or attenuation of the light transmitted through the matrix.

While the presence of nanoparticles 11 within polymer matrix material 10 does not significantly scatter the light, they can contribute to-significantly different properties, as compared to the matrix material alone. For example, as already noted, nanoparticles 11 can be made from various semiconductor materials, which can have refractive index values of between about 2 and about 5. Upon dispersion of nanoparticles 11 into polymer matrix material 10, the resulting nanocomposite material will take on an index of refraction value somewhere between the refractive index of polymer matrix material 10 (usually less than 2) and the refractive index of the nanoparticle material. The resulting refractive index of the nanocomposite material will depend on the density of nanoparticles 11 within polymer matrix material 10. For example, as the density of nanoparticles 11 in polymer matrix material 10 increases, the refractive index of the nanocomposite also generally increases.

Inclusion of nanoparticles 11 into halogenated matrix material 10, at least in one particular application, can provide a nanocomposite material useful in optical waveguide applications. For example, nanoparticles 11 allow for fabrication of a waveguide material having a particular refractive index. By tuning the refractive index in this way, transmission losses in optical waveguides resulting from refractive index mismatches in adjacent materials could be minimized. Additionally, however, because of the small size of nanoparticles 11, the nanocomposite material can retain all of the desirable transmission properties of polymer matrix material 10. In an embodiment, the index of refraction is tuned to be about 1 to about 5.

Figure 2:
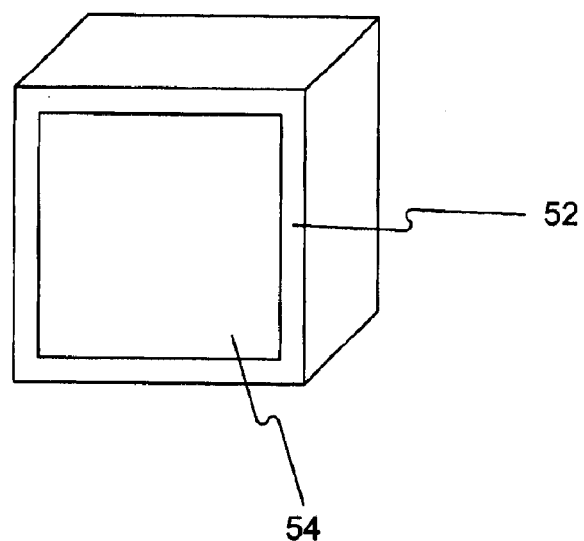
FIG. 2 depicts a schematic of an optical waveguide according to one embodiment of the invention.

FIG. 2 illustrates an optical waveguide 50 according to one embodiment of the present invention. Optical waveguide 50 includes core material 54 for transmitting radiation and cladding material 52 that promotes internal reflections. Core 54 of the optical waveguide can be formed of a nanocomposite material as illustrated, for example, in FIG. 1. Specifically, the core includes a polymer matrix and a plurality of nanoparticles dispersed within the polymer matrix. Each of the plurality of nanoparticles in optical waveguide 50 can have a refractive index between about 2 and about 5. By selecting a material having a particular index of refraction value, the overall index of refraction of core 54 of optical waveguide 50 can be tuned to a desired value. Like the nanocomposite material shown in FIG. 1, a majority of the nanoparticles present in core 54 may include a polymer outer coating layer. Further, in one embodiment of the present invention, the both the outer coating layer and the polymer matrix material of core 54 may be halogenated, advantageously fluorinated.

In addition to elements of the gain medium, still other materials are useful in creating nanoparticles 11. For example, the nanoparticles, themselves, can include a polymer. In an exemplary embodiment of the invention, the polymer nanoparticles include polymers that contain functional groups that can bind rare earth ions. Such polymers include, for example, homopolymers or copolymers of vinyl, acrylic, vinyl aromatic, vinyl esters, alpha beta unsaturated acid esters, unsaturated carboxylic acid esters, vinyl chloride, vinylidene chloride, and diene monomers. The reactive groups of these polymers can be any of the following: polyphosphates, phosphates, phosphinates, dithiophosphinates, thiophosphate, pyrophosphates, alkyl titanates, alkyl zirconates, silanes, alcohols, amines, carboxylates, amides, sulfates, sulfites, esters, acid chloride, acetylacetonate, thiols, and alkylcyanide. In addition, the polymers used to form the nanoparticles can be main chain polymers containing elements of the gain medium in the polymer backbone. Further, the polymers can be highly halogenated yet have different solubility from the host polymers. In addition, the polymer-based nanoparticles can be made from organic dye molecules or chromophores, or ionic forms of these dye molecules or chromophores for applications in electrooptic materials. Further, the polymer-based nanoparticles can be made from organic dye molecules or chromophores, or ionic forms of these dye molecules or chromophores for applications in thermooptic materials. Moreover, the polymer-based nanoparticles can be made from organic dye molecules or chromophores, or ionic forms of these dye molecules or chromophores for applications in acoustoopic materials.

In addition to elements of the gain medium, still other materials are useful in creating nanoparticles 11. For example, the nanoparticles, themselves, can include organic crystals. In an exemplary embodiment of the invention, the organic crystal nanoparticles include crystals that contain functional-groups that can bind elements of the gain medium. In addition, the organic crystals can be highly halogenated. In addition, the crystal-based nanoparticles can be made from organic dye molecules or chromophores, or ionic forms of these dye molecules or chromophores for applications in electrooptic materials. Further, the crystal-based nanoparticles can be made from organic dye molecules or chromophores, or ionic forms of these dye molecules or chromophores for applications in thermooptic materials. Moreover, the crystal-based nanoparticles can be made from organic dye molecules or chromophores, or ionic forms of these dye molecules or chromophores for applications in acoustoopic materials.

In addition to elements of the gain medium, still other materials are useful in creating nanoparticles 11. For example, the nanoparticles, themselves, can include inorganic crystals. In an exemplary embodiment of the invention, the inorganic crystal nanoparticles include lithium niobate, lithium tantalate, indium phosphide, gallium arsenide, and other electrooptic inorganic materials. Furthermore, these inorganic crystals can combine with elements of a gain medium. These crystal-based nanoparticles can be used for electrooptic, thermooptic, and acoustooptic applications.

In addition to elements of the gain medium, still other materials are useful in creating nanoparticles 11. For example, the nanoparticles, themselves, can include inorganic materials. In an exemplary embodiment of the invention, the inorganic nanoparticles include ceramic, such as lead, lanthanum zirconium titanium oxide (PLZT), and other electrooptic inorganic materials. Furthermore, these inorganic materials can combine with elements of a gain medium. These inorganic material-based nanoparticles can be used for electrooptic, thermooptic, and acoustooptic applications.

Additionally, nanoparticles 11 can be used to tune refractive index of the nanocomposite materials. Nanoparticles 11 can include a wide range of materials having various coefficient of thermal expansion (hereafter "CTE", including negative CTE)materials having negative coefficients of thermal expansion (hereinafter, "CTE"). Some of these materials include, for example, Ni—Ti alloys, $ZrW_2O_8$, $ZrMo_2O_8$, $Y_2(WO_4)_3$, V doped $ZrP_2O_7$, $ZrV_2O_7$, $(Zr_2O)(PO_4)_2$, $Th_4(PO_4)_4P_2O_7$, and $AOMO_4$, where A=Nb or Ta, and M=P, As, or V. Nanoparticles 11 formed from these materials exhibit negative CTEs. When combined with a matrix material having a positive CTE, the resulting nanocomposite material can include little, or no, expansion or contraction, even when cycled through various thermal environments..

Figure 3:
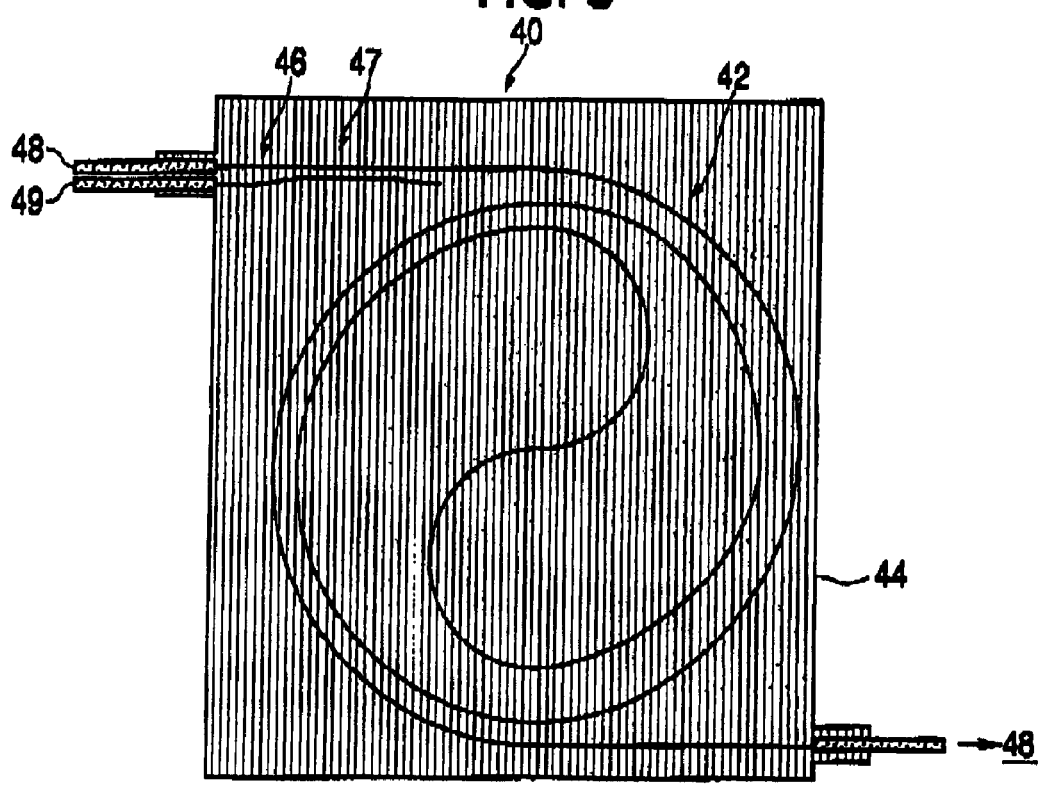
FIG. 3 depicts a schematic representation of an exemplary nanocomposite comprising several types of nanoparticles that are dispersed within a host matrix consistent with another embodiment of the invention.

Nanocomposite materials of the present invention can include more than one type of nanoparticle. For example, FIG. 3 illustrates an embodiment of the present invention in which several groups of nanoparticles 11, 21, and 31 are present within polymer matrix 10. Each group of nanoparticles 11, 21 and 31 can include a different material. It will be appreciated that individual nanoparticles can be fabricated from several different materials to form nanocomposite materials that offer benefits derived from each of the different materials. For example, use of nanoparticles 11, 21, and 31 can provide a range of different index of refraction values. Such an arrangement may be useful, for example to create broad band optical devices. It will be further appreciated that the present invention is not limited to a particular number of different types of nanoparticles dispersed within the matrix material. Rather, any number of different types of nanoparticles can be desirable depending on the particular application.

Figure 4:
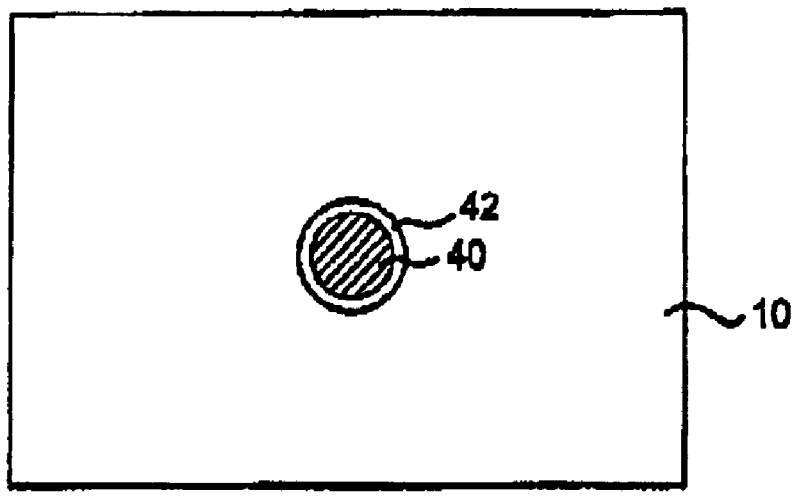
FIG. 4 depicts a schematic representation of a coated nanoparticle consistent with an embodiment of the invention.

FIG. 4 provides a schematic representation of one of nanoparticles 40 suspended within polymer matrix 10. The nanoparticle shown in FIG. 4 includes an outer coating layer 42. In one embodiment of the present invention, the outer coating layer 42 comprises a halogen containing polymer, such as fluorine. Outer coating layer 42, however, can also include other halogen-based compounds. When halogenated, the outer coating layer may be formed from at least one material chosen from halogenated polyphosphates, halogenated phosphates, halogenated phosphinates, halogenated dithiophosphinates, halogenated pyrophosphates, halogenated alkyl titanates, halogenated alkyl zirconates, halogenated silanes, halogenated alcohols, halogenated amines, halogenated carboxylates, halogenated amides, halogenated sulfates, halogenated esters, halogenated acid chloride, halogenated acetylacetonate, halogenated thiols, and halogenated alkylcyanide.

The nanoparticles according to the present invention may also include an inner coating disposed beneath the outer coating layer, wherein the inner coating includes one or more passivation layers.

Coating 42 can serve several functions. It can be used to protect the underlying nanoparticle from moisture or other potentially detrimental substances. Additionally, coating 42 can also be designed to prevent agglomeration. Agglomeration is a significant problem when making nanocomposite materials that include nanoparticles distributed within a polymer material. Because of the small size and great numbers of nanoparticles that can be distributed within a host material, there is a large amount of interfacial surface area between the surfaces of the nanoparticles and the surrounding host material. As a result, the nanoparticle-host material system attempts to minimize this interfacial surface area, and corresponding surface energy, by combining the nanoparticles together to form larger particles. This process is known as agglomeration. Once the nanoparticles have agglomerated within a host material, it is extremely difficult to separate the agglomerated particles back into individual nanoparticles.

Agglomeration of the nanoparticles within the host material can result in a nanocomposite material that lacks a desired characteristic. Specifically, when nanoparticles agglomerate together, the larger particles formed may not behave in a similar way to the smaller nanoparticles. For example, while nanoparticles can be made small enough to avoid scattering with light in the nanocomposite material, agglomerated particles may become sufficiently large to interfere with the incident light and cause scattering, resulting in excessive optical signal loss.

By selecting a coating material that is compatible with a particular host matrix material, coating 42 can eliminate the interface between the nanoparticle outer surface and host matrix 10. In this way, coating 42 effectively masks each of nanoparticles 40 from the others in the nanocomposite material. As a result, the nanoparticles do not agglomerate to minimize the interfacial surface area/surface energy that would exist between uncoated nanoparticles and host matrix material 10. In certain embodiments, therefore, coating 42 enables substantially uniform dispersion of nanoparticles 40 into host matrix material 10 without significant agglomeration.

In another exemplary embodiment of the present invention involving a halogenated polymer host matrix, the outer coating layer 42 is halogenated, and can include, for example, fluorinated silanes, fluorinated alcohols, fluorinated amines, fluorinated carboxylates, fluorinated amides, fluorinated sulfates, fluorinated esters, fluorinated acid chloride, fluorinated acetylacetonate, fluorinated thiols, and fluorinated alkylcyanide. Analogs of these materials incorporating halogens other than fluorine can also be employed in outer coating layer 42.

In addition to protecting nanoparticles 40 and suppressing agglomeration, coating 42 can also be designed to interact with the surfaces of nanoparticles 40 in a beneficial way. For example, halogenated outer coating layer 42 can include a material that reacts with and neutralizes an undesirable radical group, for example an OH or ester containing group, that can sometimes be found on the surfaces of nanoparticles 40. In this way, coating 42 can prevent the undesirable radical from reacting with halogenated polymer matrix 10.

Figure 5:
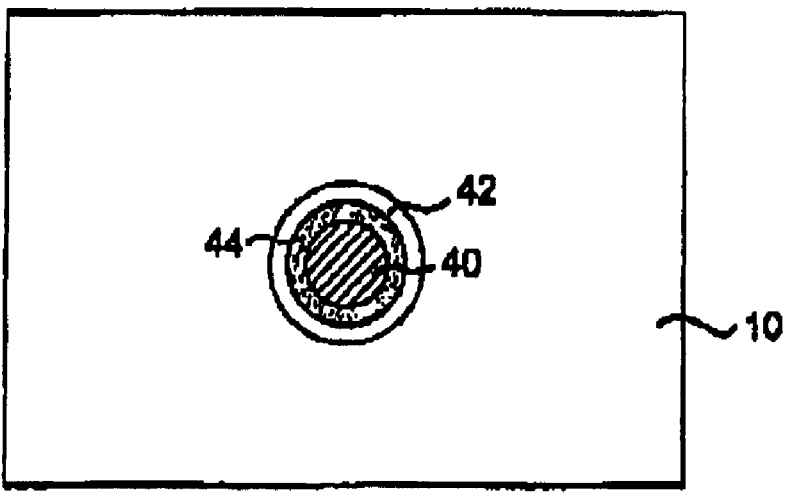
FIG. 5 depicts a schematic representation of a coated nanoparticle consistent with another embodiment of the invention.

Coatings on nanoparticles 40 are not limited to a single layer, such as halogenated outer coating layer 42 shown in FIG. 4. Rather, nanoparticles 40 can be coated with a plurality of layers. FIG. 5 provides a diagrammatic representation of one of nanoparticles 40 suspended within polymer matrix material 10. As shown, inner coating layer 44 can be disposed between one of nanoparticles 40 and outer coating layer 42. In one embodiment, inner coating layer 44 acts as a passivation layer. For example, in certain situations the interaction between a particular nanoparticle material and a particular halogenated outer coating layer may be unknown. In these situations, the nanoparticles can be coated with a passivation layer that includes a material that interacts with one or both of the nanoparticle material and the halogenated outer coating layer material in a known way. Such an inner coating layer can prevent, for example, delamination of halogenated outer coating layer 42 from the underlying nanoparticle. While inner coating layer 44 is shown in FIG. 5 as a single layer, inner coating layer 44 can include multiple layers of similar or different materials.

Nanoparticles 40 can be coated in several ways. For example, nanoparticles 40 can be coated in situ, or, in other words, during the formation process. More specifically, nanoparticles 40 can be formed in the presence of a coating material. In this,way, for example, once nanoparticles 40 have dried to form an aerosol, they may already include coating 42 of the desired material.

Additionally, coating 42 can be formed by placing the nanoparticles into direct contact with the coating material. For example, nanoparticles 40 can be dispersed into a solution including a coating material. In some instances, nanoparticles 40 can include a residual coating left over from the formation process. In these instances, nanoparticles 40 can be placed into a solvent including constituents for forming the outer layer. Once in the solvent, a chemical replacement reaction can be performed to substitute outer coating layer 42 for the preexisting coating on each of nanoparticles 40.

Inner coating layer 44, which can include one or more passivation layers, can be formed prior to formation of outer coating layer 42 using methods similar to those for forming outer coating layer 42.

Once nanoparticles 40 have been formed and coated, they can be dispersed into host matrix 10. To obtain a substantially uniform distribution of nanoparticles 40 within host matrix 10, a high shear stress mixer can be used. Examples of a high shear stress mixer are a homogenizer and a jet mixer.

According to yet another aspect of the present invention, a microresonator is provided that comprises, a nanoparticle composite material, as described above, having a shape that is bounded at least in part by a reflecting surface in which electromagnetic radiation having a discrete frequency can set up a standing wave mode. Methods for fabricating microresonators are also provided.

Figure 6:
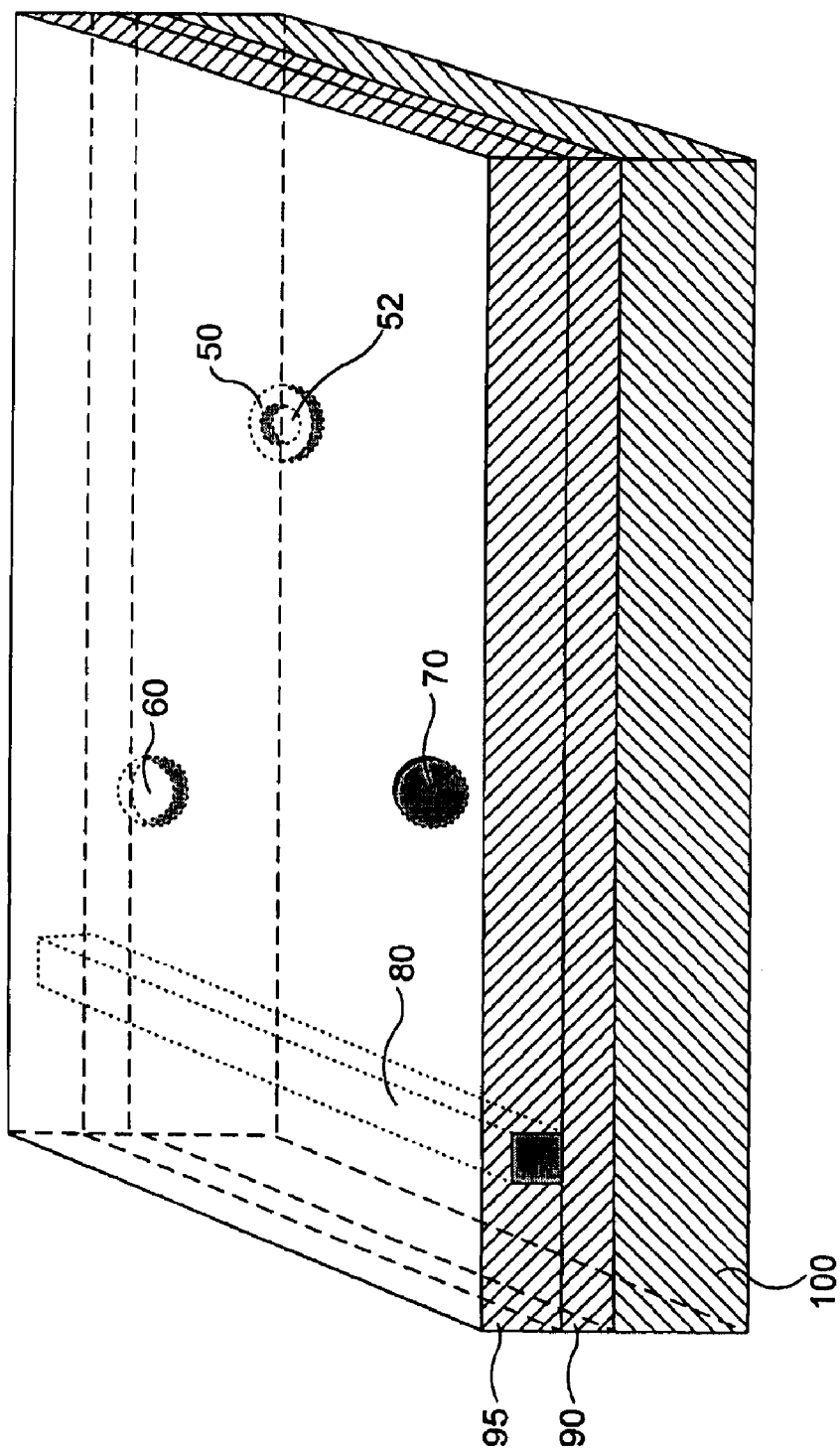
FIG. 6 depicts a perspective view of several microresonators that can be constructed according to this invention, including a microring, a microdisk, a microsphere, and a microline consistent with the invention.

As shown in FIG. 6, a microresonator according to this invention can be, for example, microring 50, microdisk 60, microsphere 70, and microline 80. As used herein, a microring resonator is any resonanating device that has a closed-loop shape. A common closed-loop shape is a symmetric torus, but it will be appreciated that other closed loop shapes, such as a "figure-eight" or an asymmetric torus, can also work.

In contrast to microring 50, which has unused center portion 52, microdisk 60 has no such portion. A microdisk resonator is solid and can take the form, for example, of a circular,ellipsoidal, or polygon, planar disk. Microsphere resonator 70 is generally defined by its spherical symmetry, but it will be appreciated that other shapes, such as asymmetric ellipsoids, are also included. Microline resonator 80 is any substantially one-dimensional waveguide that has a length that is appropriate to induce resonation. For example, a conventional laser can be constructed from a linear microcavity, such as microline resonator 80. A microplate is any resonator having a substantially fixed thickness and a two-dimensional shape that sets up one or more appropriate standing wave modes.

It will be appreciated that the resonators shown in FIG. 6 are not to scale and are embedded between lower and upper cladding layers 90 and 95, respectively. As shown, lower cladding layer 90 can be disposed on substrate 100. It will be further appreciated that in some applications, cladding layers may be unnecessary and that air, for example, can be used as cladding.

As discussed above, the nanocomposite material used to form a resonator according to this invention can have very high refractive indices, generally between about 2 and about 5, but even a higher refractive index is possible using appropriate types and concentrations of nanoparticles. As mentioned above, cladding layers can be formed from any material having a relatively low refractive index to facilitate, as much as possible, total internal reflection of light at the core-cladding interface.

When the difference between the refractive indices of the core and cladding materials is large, a resonator can be fabricated with a small turning radius. Thus, core materials according to this invention that have a relatively high refractive index (e.g., between about 2 and about 5) when combined with cladding materials that have a relatively low refractive index can be particularly useful in fabricating microring, microdisk, and microsphere resonators with very small dimensions. Polymer cladding materials according to this invention generally have refractive indicies between about 1 and about 1.5, and more typically between about 1.28 and about 1.40.

The polymer matrix material, such as a halogenated polymer previously described, enables conventional photolithographic techniques to be used. Such techniques enable the fabrication of microring resonator devices with relatively smooth core-cladding interfaces, thereby obtaining low loss waveguides and enabling large Q-factors of up to about 10,000 and higher.

Figure 7:
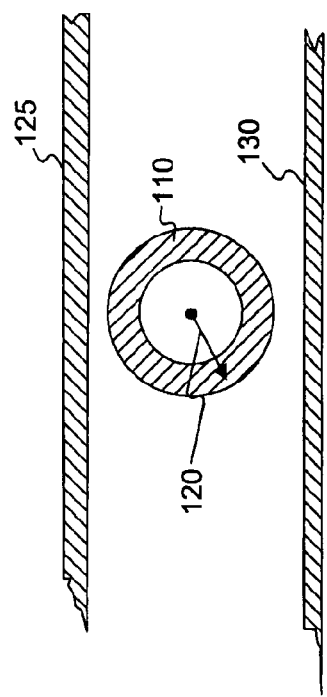
FIG. 7 depicts a top plan view of microring resonator and two waveguides consistent with the invention.

FIG. 7 shows a top plan view of microring resonator 110 having radius 120. For illustrative simplicity, cladding layers are not shown. Waveguides 125 and 130 are located adjacent to microring resonator 110 and positioned sufficiently close to resonator 110 to allow evanescent couplings therebetween. Waveguides 125 and 130 can be located in the same plane that resonator 110 resides (as shown). Alternatively, waveguides 125 and 130 can be located in planes that are different from resonator 110.

Figure 8:
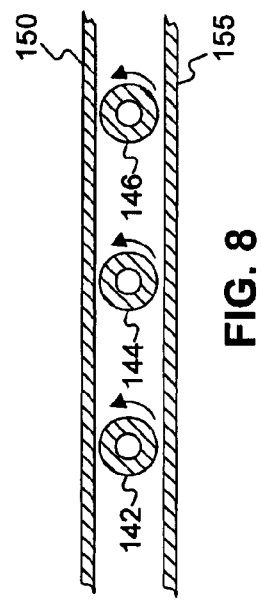
FIG. 8 depicts a top plan view of three microring resonators that are not coupled to each other but are located between and coupled to two waveguides consistent with the invention.

Multiple microring resonators can be used together to improve filter or switching performance. For example, FIG. 8 shows three microring resonators 142, 144, and 146 located between and coupled to substantially parallel waveguides 150 and 155. As described more fully by Little et al., this type of arrangement uses multilple uncoupled resonators. That is, resonator 142, 144, and 146 are not coupled to each other, but each is coupled to waveguides 150 and 155.

Figure 9:
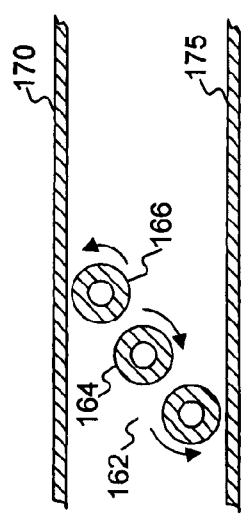
FIG. 9 depicts a top plan view of three microring resonators that are coupled to each and to two waveguides consistent with this invention.

Alternatively, multiple coupled microring resonators can be used. For example, FIG. 9 shows three coupled microring resonators 162, 164, and 166 located between substantially parallel waveguides 170 and 175. As also described more fully by Little et al., this type of arrangement couples resonator 162 to waveguide 175 and couples resonator 166 to waveguide 170. Intermediate microring resonator 164 is not coupled to either waveguide, but is coupled in series to microring resonators 162 and 166.

It will be appreciated that the number of microring resonators need not be three. Additional microring resonators, for example, can be used to form higher order filters with larger effective Q-factors. Also, consistent with this invention, microring resonators can be coupled to each other or to optical waveguides using any conventional coupling technique, including particularly evanescent coupling techniques.

The size of a microring resonator according to this invention depends on the desired operational optical frequency and the limitations of the fabrication techniques available. For example, microring resonators according to this invention can have any useful radius (i.e., radius 120 of FIG. 7), including a radius between about 1 micron and about 25 microns, and particularly between about 2.5 microns and about 10 microns. Also, the cross sectional dimension of the core is typically between about 0.1 micron and about 5 microns, and usually between about 0.2 micron and about 1 micron, although this dimension is subject to material and fabrication design constraints.

The core of a microresonator, such as a microring resonator, according to this invention can include optically active particles that can be activated, or selected, to slowly or abruptly change a physical or optical property of the resonator. For example, optically active particles (that exhibit nonlineaer optical, thermoelectric, or electrooptical properties) could be added to the nanocomposite material, cladding material, or even a substrate material.

If optically active particles in the core or cladding material of a microring resonator are selectively absorptive, for example, the resonator can be selectively turned on and off. When a microring resonator includes optically active particles (e.g., lithium niobate, electrooptic organic chromophores, etc.) in either its core or its cladding, the resonator can be selectively switched on or off by selectively applying an electric field via independently controllable local electrodes that may be located above and below the microring. In this way, high speed modulators can be fabricated.

Alternatively, because a microring resonator is very sensitive to changes in its physical dimensions, one can switch a resonator by-changing the microring resonator's temperature by heating or cooling the resonator if it has a non-zero CTE. Heating can be achieved, for example, by adding a resistive heating element near a microring resonator, such as on an adjacent substrate. It is possible to increase the CTE of the microring in a number of ways. First, one can add particles having a large positive or negative CTE directly to the core material, however, to avoid scattering effects, those particles must be made very small. Second, one can select a cladding material that has a large inherent CTE or an enhanced CTE through the addition of large CTE ingredients. Finally, one can add materials having a large CTE to the substrate. In this way, one does not increase scattering within the core or at the interface between the core and the cladding layer.

Figure 10:
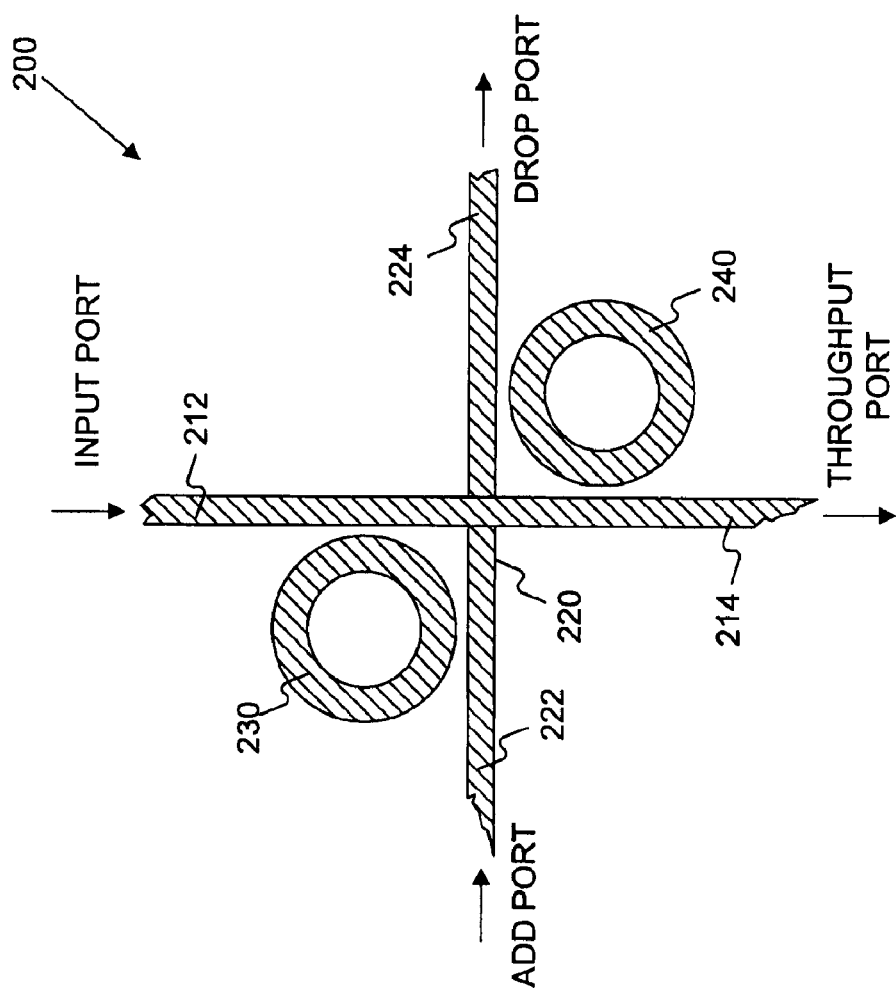
FIG. 10 depicts a planar view of an add/drop optical filter that can be fabricated consistent with this invention.

FIG. 10 shows a planar view of add/drop optical filter 200 that can be built according to this invention. Filter 200 includes waveguide 210 having input port 212 and through-put port 214, waveguide 220 having add port 222 and drop port 224, and pair of microring resonators 230 and 240. As shown, waveguides 210 and 220 physically cross. Microring resonators 230 and 240 are coupled to waveguides 210 and 220. Consistent with this invention, both resonators include a nanocomposite material that includes a random glassy matrix, such as an inorganic glass and amorphous organic polymer, and a plurality of nanoparticles dispersed within the matrix, and wherein a majority of the nanoparticles includes an outer coating layer. Operation of such a filter is described in detail by Chu et al. "Second-Order Filter Response From Parallel coupled Glass Microring Resonators" *IEEE Photonics Technology Letters,* Vol. 11, No. 11, at 1426 (November 1999), which is hereby incorporated by reference in its entirety.

Figure 11:
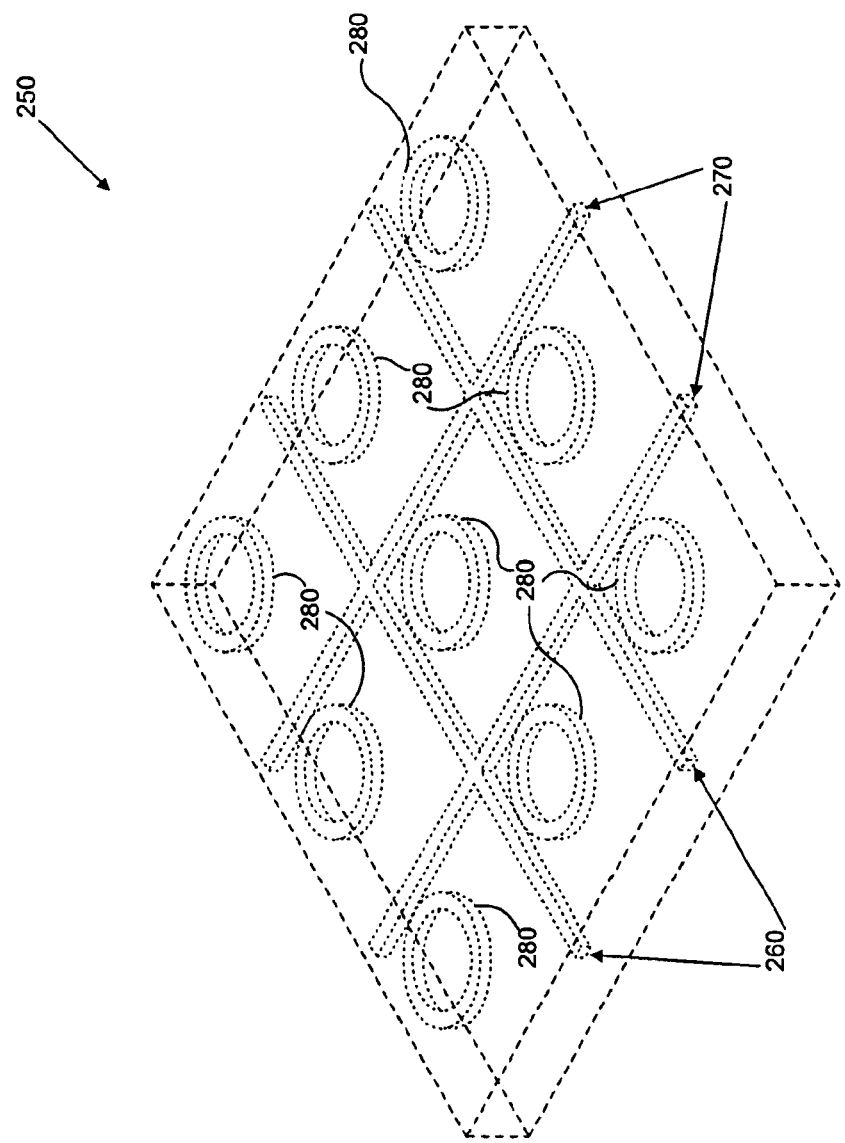
FIG. 11 depicts a perspective view of an integrated optical switch array circuit that can be fabricated consistent with this invention.

FIG. 11 shows a perspective view of integrated optical switch array circuit 250 that can be fabricated according to this invention. Circuit 250 includes plurality of light-transmitting waveguides 260 on a planar lightwave circuit, plurality of light-transmitting waveguides 270 that cross-connect with plurality of waveguides 270, and plurality of microring resonators 280 for selectively optically coupling pluralities of waveguides 260 and 270. Consistent with this invention, each of the microring resonators 280 includes a core formed from a nanocomposite material that includes a random glassy matrix and a plurality of nanoparticles dispersed within the host matrix, wherein a majority of the nanoparticles has an outer coating layer.

It will be appreciated that circuit 250 can be fabricated so that it operates passively or actively. For passive operation, each microring can be designed to perform a particular coupling or filtering function, such as in the case of a WDM multiplexer or demultiplexer device. Alternatively, the device can be made active by including electrodes, or thermal elements near each of the microrings, depending on whether the microrings are designed to be electrooptically or thermally active. Then, when optical fibers are coupled to the waveguides, circuit 250 acts like a switch array.

Figure 12:
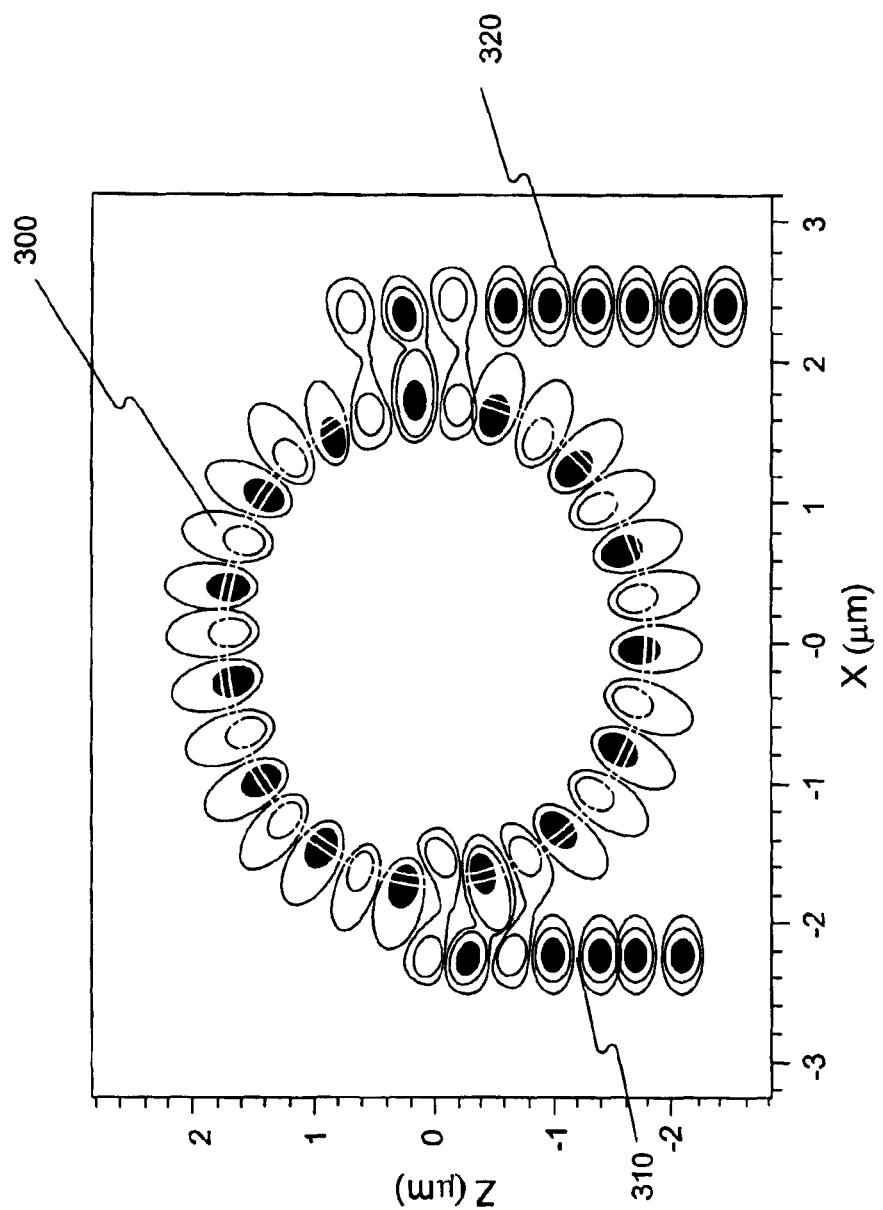
FIG. 12 depicts a top planar view of a computer simulation of the instantaneous electric fields that exist in an illustrative microring resonator and in two waveguides that are coupled to opposite ends of the resonator at resonance consistent with this invention.

FIG. 12 shows a top planar view of a computer simulation of the instantaneous electric fields that exist in illustrative microring resonator 300 consistent with this invention and in two waveguides 310 and 320 that are coupled to opposite ends of resonator 300 at resonance. Waveguide 310 has input port 312 and output port 314 and waveguide 320 has input port 322 and 324. It will be appreciated that input port 312 and output port 324 can be located at the ends of waveguides 310 and 320, respectively, or along their lengths. Also, operation of the resonator can be reversed so that input and output ports perform functions that are opposite their nominal functions. Microring resonator 300 can be used as an add/drop filter or a switch.

Consistent with yet another aspect of this invention, a method for fabricating a microresonator is provided. Once again, the microresonator comprises a nanocomposite material bound at least in part by a reflecting surface in which electromagnetic radiation having a discrete frequency can set up a standing wave mode. The method can include (1) disposing an undercladding layer on a substrate, (2) disposing a film of a nanocomposite material on the undercladding layer, (3) processing the nanocomposite material to form the microresonator shape, and disposing an overcladding layer on the shaped nanocomposite material. As discussed above, the reflectivity of the core-cladding interface depends at least in part on the refractive index difference between the core and cladding materials. In one embodiment, the processing step includes photolithographically defining the resonator core shape in the film of nanocomposite material and then etching the film to form the desired shape.

One skilled in the art will appreciate that the present invention can be practiced by other than the described embodiments, which are presented for purposes of illustration and not of limitation, and the present invention is limited only by the claims which follow.

What is claimed is:

1. A microresonator comprising a nanocomposite material, said nanocomposite material comprising:
    a random glassy host matrix; and
    a plurality of nanoparticles dispersed within the random glassy host matrix,
wherein said microresonator has a shape sufficient to allow electromagnetic radiation having selected frequencies to set up a standing wave mode.

2. The microresonator of claim 1, further comprising a reflecting surface adjacent to and defining said shape.

3. The microresonator of claim 1, wherein said shape is chosen from a microring, a microdisk, a microsphere, a microplate, and a microline.

4. The microresonator of claim 3, wherein the shape is a first microring having a core.

5. The microresonator of claim 4, further comprising a first cladding disposed on the core.

6. The microresonator of claim 5, wherein said first cladding comprises a material having a refractive index less than the refractive index of the composite material.

7. The microresonator of claim 6, wherein said first cladding has a refractive index ranging from about 1.0 to about 1.5.

8. The microresonator of claim 6, wherein said first cladding has a refractive index ranging from about 1.28 to about 1.40.

9. The microresonator of claim 4, further comprising a second microring coupled to the first microring, wherein the second microring comprises:
    a second core; and
    a second cladding disposed on the second core.

10. The microresonator of claim 9, wherein the first microring and second microring are coupled together through an evanescent coupling.

11. The microresonator of claim 4, wherein said microring is coupled to at least one waveguide.

12. The microresonator of claim 11, wherein the first microring and the at least one waveguide are evanescently coupled.

13. The microresonator of claim 4, wherein the first microring has a radius ranging from about 1 micron to about 25 microns.

14. The microresonator of claim 13, wherein the radius ranges from about 2.5 microns to about 10 microns.

15. The microresonator of claim 4, wherein said core has a cross sectional dimension ranging from about 0.1 micron to about 5 microns.

16. The microresonator of claim 15, wherein said core has a cross sectional dimension ranging from about 0.2 micron to about 1 micron.

17. The microresonator of claim 1, wherein said nanocomposite material has a refractive index between about 1.5 and about 5.

18. The microresonator of claim 1, wherein said nanocomposite material further comprises optically active particles.

19. The microresonator of claim 18, wherein the optically active particles are present in an amount sufficient to selectively alter an optical property of the resonator.

20. The microresonator of claim 19, wherein the resonator is a microring and the optical property is chosen from (1) the selected frequency that can set up the standing wave mode, (2) Q-factor, (3) overall dimension, and (4) free spectral range.

21. The microresonator of claim 1, wherein the plurality of nanoparticles is substantially uniformly distributed within the random glassy host matrix.

22. The microresonator of claim 1, wherein the concentration of nanoparticles ranges from about 0 volume % to about 20 volume %.

23. The microresonator of claim 1 wherein a majority of said nanoparticles includes an outer coating layer.

24. The microresonator of claim 23 wherein said outer coating layer comprises a polymer.

25. The microresonator of claim 24, wherein the halogenated outer coating layer is formed from at least one material chosen from halogenated polyphosphates, halogenated phosphates, halogenated phosphinates, halogenated dithiophosphinates, halogenated pyrophosphates, halogenated alkyl titanates, halogenated alkyl zirconates, halogenated silanes, halogenated alcohols, halogenated amines, halogenated carboxylates, halogenated amides, halogenated sulfates, halogenated esters, halogenated acid chloride, halogenated acetylacetonate, halogenated thiols, and halogenated alkylcyanide.

26. The microresonator of claim 24, wherein the halogenated outer coating layer is fluorinated.

27. The microresonator of claim 24, wherein said plurality of nanoparticles further includes an inner coating disposed beneath the halogenated outer coating layer, wherein the inner coating includes one or more passivation layers.

28. The microresonator of claim 24, wherein the halogenated outer coating layer comprises a material that reacts with and neutralizes a radical group on at least one of the plurality of nanoparticles.

29. The microresonator of claim 28, wherein the radical group is OH.

30. The microresonator of claim 28, wherein the radical group comprises an ester.

31. The microresonator of claim 23 wherein said outer coating layer comprises a halogenated polymer.

32. The microresonator of claim 23 wherein said outer coating layer comprises fluorinated silanes, fluorinated alcohols, fluorinated amines, fluorinated carboxylates, fluorinated amides, fluorinated sulfates, fluorinated esters, fluorinated acid chloride, fluorinated acetylacetonate, fluorinated thiols, and fluorinated alkylcyanide, and analogs of these materials incorporating halogens other than fluorine.

33. The microresonator of claim 23 wherein said outer coating layer comprises inorganic materials.

34. The microresonator of claim 1, wherein said random glassy host matrix is chosen from inorganic glasses.

35. The microresonator of claim 34, wherein said inorganic glasses are chosen from doped and undoped silica.

36. The microresonator of claim 35, wherein said inorganic glasses are chosen from aluminosilicate glasses, silica, germania-silica, lithium-alumina-silica, sulfide glasses, phosphate glasses, halide glasses, oxide glasses, and chalcogenide glasses.

37. The microresonator of claim 35, wherein said random glassy host matrix is chosen from polymethylmethacrylates, polystyrenes, polycarbonates, polyimides, epoxy resins, cyclic olefin copolymers, cyclic olefin polymers, acrylate polymers, polyethylene teraphthalate, polyphenylene vinylene, polyether ether ketone, poly (N-vinylcarbazole), acrylonitrile-styrene copolymer, polyetherimide poly (phenylenevinylene).

38. The microresonator of claim 35, wherein said random glassy host matrix is chosen from polymers containing the following functional groups: polyphosphates, phosphates, phosphinates, dithiophosphinates, thiophosphate, pyrophosphates, alkyl titanates, alkyl zirconates, silanes, alcohols, amines, carboxylates, amides, sulfates, sulfites, esters, acid chloride, acetylacetonate, thiols, and alkylcyanide.

39. The microresonator of claim 35, wherein said random glassy host matrix is chosen from halogenated polymers.

40. The microresonator of claim 1, wherein said random glassy host matrix is chosen from homopolymers, copolymers, terpolymers, cross-linked polymers, and blends of polymers.

41. The microresonator of claim 1, wherein said random glassy host matrix is chosen from halogenated elastomers, perhalogenated elastomers, halogenated plastics, and perhalogenated plastics.

42. The microresonator of claim 1, wherein said random glassy host matrix comprises a polymer, a copolymer, a terpolymer, or cross-linked polymer having at least one halogenated monomer chosen from one of the following formulas:

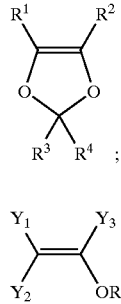
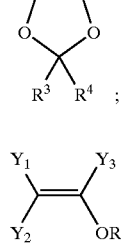
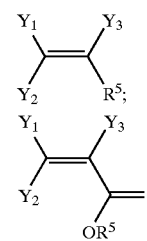

wherein,
$R^1$, $R^2$, $R^3$, $R^4$, and $R^5$, which may be identical or different, are each chosen from linear or branched hydrocarbon-based chains, capable of forming at least one carbon-based ring, being saturated or unsaturated, wherein at least one hydrogen atom of the hydrocarbon-based chains may be halogenated; a halogenated alkyl, a halogenated aryl, a halogenated cyclic alky, a halogenated alkenyl, a halogenated alkylene ether, a halogenated siloxane, a halogenated ether, a halogenated polyether, a halogenated thioether, a halogenated silylene, and a halogenated silazane;

$Y_1$ and $Y_2$, which may be identical or different, are chosen from H, F, Cl, and Br atoms; and $Y_3$ is chosen from H, F, Cl, and Br atoms, $CF_3$, and $CH_3$.

43. The microresonator of claim 42, wherein $R^1$, $R^2$, $R^3$, $R^4$, and $R^5$ are at least partially fluorinated.

44. The microresonator of claim 42, wherein $R^1$, $R^2$, $R^3$, $R^4$, and $R^5$ are completely fluorinated.

45. The microresonator of claim 42, wherein at least one of $R^1$, $R^2$, $R^3$, $R^4$, and $R^5$ is chosen from a $C_1$–$C_{10}$, linear or branched, being saturated or unsaturated hydrocarbon-based chains.

46. The microresonator of claim 42, wherein said random glassy host matrix comprises a polymer condensation product of at least one of the following monomeric reactions:

$$HO\text{—}R\text{—}OH + NCO\text{—}R'\text{—}NCO;$$

or

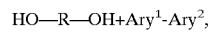

wherein
R, R', which may be identical or different, are chosen from one of halogenated alkylenes, halogenated siloxanes, halogenated ethers, halogenated silylenes, halogenated arylenes, halogenated polyethers, and halogenated cyclic alkylenes; and $Ary^1$, $Ary^2$, which may be identical or different are chosen from halogenated aryls and halogenated alkyl aryls.

47. The microresonator of claim 42, wherein said random glassy host matrix comprises a material chosen from halogenated polycarbonates, halogenated cyclic olefin polymers, halogenated cyclic olefin copolymers, halogenated polycyclic polymers, halogenated polyimides, halogenated polyether ether ketones, halogenated epoxy resins, and halogenated polysulfones.

48. The microresonator of claim 42, wherein said random glassy host matrix comprises a combination of two or more different fluoropolymer materials.

49. The microresonator of claim 42, wherein said random glassy host matrix further comprises halogenated polymers having functional groups chosen from phosphinates, phosphates, carboxylates, silanes, siloxanes, and sulfides.

50. The microresonator of claim 49, wherein the functional groups are chosen from POOH, POSH, PSSH, OH, $SO_3H$, $SO_3R$, $SO_4R$, COOH, $NH_2$, NHR, $NR_2$, $CONH_2$, and $NH\text{—}NH_2$, wherein R denotes: linear or branched hydrocarbon-based chains, capable of forming at least one carbon-based ring, being saturated or unsaturated; alkylenes, siloxanes, silanes, ethers, polyethers, thioethers, silylenes, and silazanes.

51. The microresonator of claim 42, wherein at least one material comprising said random glassy host matrix is chosen from homopolymers, or copolymers, of vinyl, acrylate, methacrylate, vinyl aromatic, vinyl ester, alpha beta unsaturated acid ester, unsaturated carboxylic acid ester, vinyl chloride, vinylidene chloride, and diene monomers.

52. The microresonator of claim 42, wherein said random glassy host matrix comprises a hydrogen-containing fluoroelastomer.

53. The microresonator of claim 42, wherein said random glassy host matrix further comprises a cross-linked halogenated polymer.

54. The microresonator of claim 53, wherein said halogenated polymer comprises a fluorinated polymer.

55. The microresonator of claim 53, wherein said random glassy host matrix comprises a perhalogenated polymer.

56. The microresonator of claim 55, wherein the perhalogenated polymer comprises a perfluorinated polymer.

57. The microresonator of claim 55, wherein the perhalogenated polymer comprises a perhalogenated elastomer.

58. The microresonator of claim 42, wherein said random glassy host matrix comprises at least one of a hydrogen-containing fluoroelastomer, or a hydrogen-containing fluoroplastic.

59. The microresonator of claim 42, wherein said random glassy host matrix comprises a blend of at least one material chosen from halogenated, fluorinated, and perfluorinated polymer.

60. The microresonator of claim 42, wherein said random glassy host matrix comprises poly[2,2-bistrifluoromethyl-4,5-difluoro-1,3-dioxole-co-tetrafluoroethylene].

61. The microresonator of claim 42, wherein said random glassy host matrix comprises poly[2,2-bisperfluoroalkyl-4,5-difluoro-1,3-dioxole-co-tetrafluoroethylene].

62. The microresonator of claim 42, wherein said random glassy host matrix comprises poly[2,3-(perfluoroalkenyl) perfluorotetrahydrofuran].

63. The microresonator of claim 42, wherein said random glassy host matrix comprises poly[2,2,4-trifluoro-5-trifluoromethoxy-1,3-dioxole-co-tetrafluoroethylene].

64. The microresonator of claim 42, wherein said random glassy host matrix comprises poly(pentafluorostyrene).

65. The microresonator of claim 42, wherein said random glassy host matrix comprises fluorinated polyimide.

66. The microresonator of claim 42, wherein said random glassy host matrix comprises fluorinated polymethylmethacrylate.

67. The microresonator of claim 42, wherein said random glassy host matrix comprises polyfluoroacrylates.

68. The microresonator of claim 42, wherein said random glassy host matrix comprises polyfluorostyrene.

69. The microresonator of claim 42, wherein said random glassy host matrix comprises fluorinated polycarbonates.

70. The microresonator of claim 42, wherein said random glassy host matrix comprises perfluoro-polycyclic polymers.

71. The microresonator of claim 42, wherein said random glassy host matrix comprises fluorinated cyclic olefin polymers.

72. The microresonator of claim 42, wherein said random glassy host matrix comprises fluorinated copolymers of cyclic olefins.

73. The microresonator of claim 1, wherein said plurality of nanoparticles comprises at least one element chosen from transition metal elements, rare-earth metal elements, group VA elements, semiconductors, and group IVA elements in the forms of ions, alloys, compounds, composites, complexes, chromophores, dyes or polymers.

74. The microresonator of claim 73, wherein said at least one element is combined with at least one material chosen from oxides, phosphates, halophosphates, arsenates sulfates, borates, aluminates, gallates, silicates, germinates, vanadates, niobates, tantalates, tungstates, molybdates, alkalihalogenates, halides, nitrides, nitrates, sulfides, zirconates, selenides, sulfoselenides, oxysulfides, phosphinates, hexafluorophosphinates, and tetrafluoroborates.

75. The microresonator of claim 73, wherein said at least one element is chosen from $Er^{3+}$, $Dy^{3+}$, $Nd^{3+}$, $Pr^{3+}$, $V^{2+}$, $V^{3+}$, $Cr^{3+}$, $Cr^{4+}$, $Co^{2+}$, $Fe^{2+}$, $Ni^{2+}$, $Ti^{3+}$, and $Bi^{3+}$, and is combined with at least one material chosen from oxides, phosphates, halophosphates, arsenates, sulfates, borates, aluminates, gallates, silicates, germinates, vanadates, niobates, tantalates, tungstates, molybdates, alkalihalogenates, halides, nitrides, nitrates, sulfides, zirconates, selenides, sulfoselenides, oxysulfides, phosphinates, hexafluorophosphinates, and tetrafluoroborates.

76. The microresonator of claim 73, wherein said plurality of nanoparticles comprises a semiconductor material.

77. The microresonator of claim 76, wherein said semiconductor material chosen from Si, PbS, Ge, GaP, GaAs, InP, InAs, InSb, PbSe, ZnS, PbS, and PbTe.

78. The microresonator of claim 73, wherein said plurality of nanoparticles comprises at least one material chosen from group IIIA through group VA elements.

79. The microresonator of claim 73, wherein said plurality of nanoparticles comprises at least one material chosen from transition metal elements, transition metal complexes, transition metal containing materials, transition metal oxides, and transition metal containing polymers.

80. The microresonator of claim 73, wherein said plurality of nanoparticles comprises at least one material having an index of refraction ranging from about 1 to about 5.

81. The microresonator of claim 73, wherein said plurality of nanoparticles comprises at least one material having an index of refraction ranging from about 1.5 to about 4.5.

82. The microresonator of claim 73, wherein said plurality of nanoparticles comprises at least one material chosen from dye nanoparticles.

83. The microresonator of claim 73, wherein said plurality of nanoparticles further comprises at least one material chosen from Si, PbS, Ge, GaP, GaAs, InP, ZnS, PbS, InAs, InSb, PbSe, PbTe, lithium niobate, non-linear optical chromophores, and organic dyes.

84. The microresonator of claim 73, wherein said plurality of nanoparticles comprises at least one functional group is chosen from POOH, POSH, OH, $SO_3H$, $SO_3R$, $SO_4R$, COOH, $NH_2$, NHR, $NR_2$, $CONH_2$, and $NH-NH_2$, wherein R is chosen from linear or branched hydrocarbon-based chains, capable of forming at least one carbon-based ring, being saturated or unsaturated, alkylenes, siloxanes, silanes, ethers, polyethers, thioethers, silylenes, and silazanes.

85. The microresonator of claim 73, wherein said plurality of nanoparticles comprises at least one polymer.

86. The microresonator of claim 85, wherein said at least one polymer is chosen from homopolymers, or copolymers, of vinyl, acrylic, vinyl aromatic, vinyl esters, alpha beta unsaturated acid esters, unsaturated carboxylic acid esters, vinyl chloride, vinylidene chloride, and diene monomers.

87. The microresonator of claim 1, wherein a majority of said plurality of nanoparticles has a major dimension of less than about 50 nm.

88. The microresonator of claim 1, wherein said plurality of nanoparticles further comprises a first group of particles including an active material of a first type and at least one group of particles that include an active material of a type different from the first type.

89. The microresonator of claim 1, wherein said random glassy host matrix has little, or no, optical absorption loss including electronic, vibrational, or coupled electronic-vibrational excitations induced loss.

90. The microresonator of claim 1, wherein said random glassy host matrix is an amorphous material with little, or no, microporous structure and consequent optical scattering loss.

91. The microresonator of claim 1, wherein said random glassy matrix exhibits little, or no, polarization dependence behavior, including material birefringence.

* * * * *